United States Patent [19]

Joannic et al.

[11] Patent Number: 4,513,001
[45] Date of Patent: Apr. 23, 1985

[54] β-ADRENERGIC 1-[1-BENZIMIDAZOLYL]-N-[2-(4-HYDROXY-3-METHOXY-PHENYL)-2-HYDROXY-ETHYL]-3-AMINO BUTANE AND SALTS AND HYDRATES THEREOF

[75] Inventors: Michel Joannic, Neuilly-sur-Marne; Francoise Roquet; Marcel Pesson, both of Paris, all of France

[73] Assignee: Laboratoire Roger Bellon, Neuilly sur Seine, France

[21] Appl. No.: 477,680

[22] Filed: Mar. 22, 1983

[30] Foreign Application Priority Data

Mar. 24, 1982 [FR] France ................... 82 05035

[51] Int. Cl.$^3$ ................... A61K 31/415; C07D 235/06
[52] U.S. Cl. ................... 514/394; 548/333; 514/826
[58] Field of Search ............ 548/333; 424/273 B

[56] References Cited

U.S. PATENT DOCUMENTS 3,905,990 9/1975 Ehrmann et al. ............ 548/333

FOREIGN PATENT DOCUMENTS 0008653 3/1980 European Pat. Off. .
0034116 8/1981 European Pat. Off. .

Primary Examiner—Richard A. Schwartz

[57] ABSTRACT

Novel compounds with β-adrenergic properties comprising 1-[1-benzimidazolyl] N-[2-(4-hydroxy 3-methoxy phenyl) 2-hydroxy ethyl]3-amino butane, corresponding to the following formula

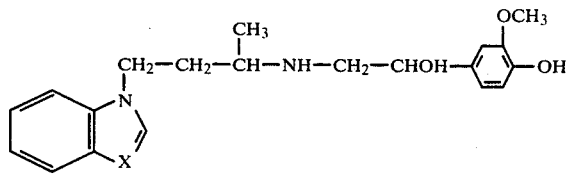

as well as its addition salts with pharmaceutically acceptable non-toxic inorganic or organic acids, and the hydrates of said salts. These compounds are particularly useful for the treatment of asthma and in the case of premature labor.

8 Claims, No Drawings

β-ADRENERGIC 1-[1-BENZIMIDAZOLYL]-N-[2-(4-HYDROXY-3-METHOXY-PHENYL)-2-HYDROXY-ETHYL]-3-AMINO BUTANE AND SALTS AND HYDRATES THEREOF

The present invention relates to 1-[1-benzimidazolyl]N-[2-(4-hydroxy-3-methoxy-phenyl)-2-hydroxy-ethyl]-3-amino butane of formula (I), its pharmaceutically acceptable, non-toxic, inorganic or organic acid addition salts and the hydrates of said salts, having remarkable β-adrenergic properties and capable of therapeutic uses:

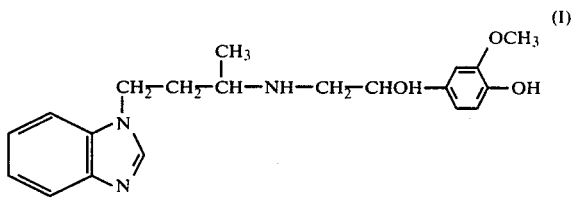

The compound (I) being dibasic, gives with acids, several types of salts, whose physicochemical characteristics may render therapeutic use more or less easy.

In general, it is possible to define an acid by the formula $AH_{n'}$, where A represents an inorganic or organic radical and H an acid proton, n' is a whole number (in the case of monoacids, n'=1; in the case of diacids, n'=2).

According to the nature of the acids and the degree of salification, the salts of the compound (I) correspond to the general formula (II), where n and n'' represent whole numbers:

The "neutral" salts in which, for the monoacids (n'=1), n=1 and n''=2; in the case of diacids (n'=2), n=1 and n''=1.

The "basic" salts, in which, for the monoacids (n'=1), n=1 and n''=1; in the case of the diacids (n'=2), n=2, n''=1.

These salts, whatever their type, can form hydrates. They can also be solvated by lower alcohols (such as methanol or ethanol), which are often employed for their preparation or their purification.

As non-toxic acid addition salts of the product of formula I according to the invention, may be cited particularly the salts with the following mineral acids: hydrochloric acid, hydrobromic acid, sulphuric acid, phosphoric acid, and the salts with the following organic acids: maleic acid, fumaric acid, tartaric acid, citric acid, oxalic acid, succinic acid, mandelic acid, methane sulfonic acid, benzene sulfonic acid, p.toluene sulfonic acid, camphosulfonic acid, etc.

Certain salts can be solvated by recrystallization solvents, and it is hence preferable to select an acid so that the corresponding salt is not solvated.

The compound according to the invention and its salts, where A represents a radical not reducible by catalytic hydrogenation, are prepared by the following steps:

(a) 3-amino-1-[1-benzimidazolyl]butane (III) (1 mole) is condensed, by a process known in itself, in an alcoholic medium, with (3-methoxy-4-phenylmethoxy)-phenylglyoxal ($IV_a$) (1-1,1 mole), or its ethyl acetal ($IV_b$) [2-ethoxy-2-hydroxy-1-(3-methoxy-4-phenylmethoxy-phenyl)ethanone] (1-1,1 mole). This reaction results in an imine (V), which is not isolated, and is reduced "in situ" by a known process, by an excess (2 to 4 moles) of sodium borohydride.

This reduction bears at the same time on the imine function and on the ketonic carbonyl group. In this way 1-[1-benzimidaxolyl]-N-[2-hydroxy-2-(3-methoxy-4-phenylmethoxy-phenyl)-ethyl]-3-amino butane (VI) is obtained.

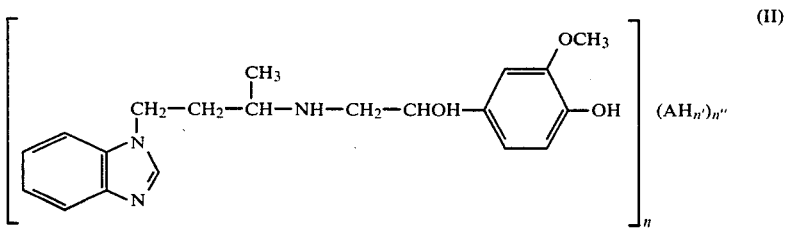

Distinction is thus made between:

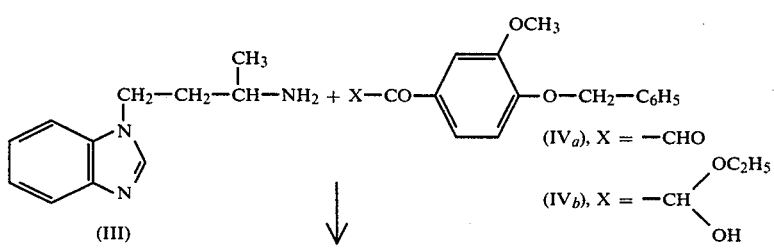

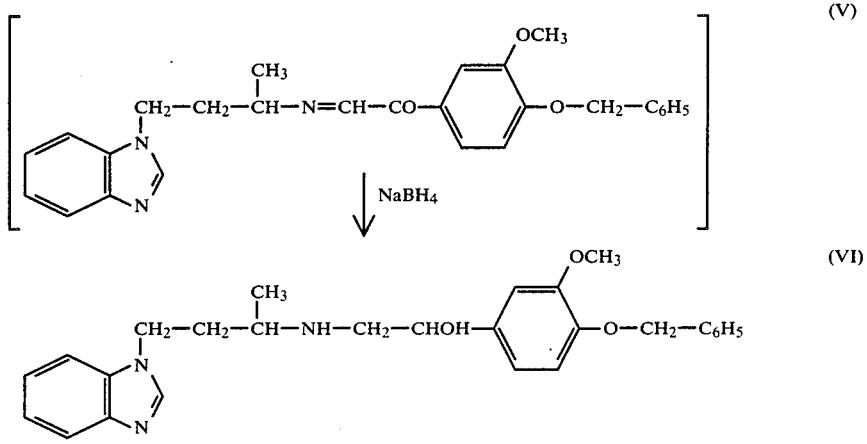

(b) The oily base (VI), is converted into a crystalline salt (VII).

(c) Hydrogenolysis of the latter provides the corresponding salt of the product according to the invention. This operation is carried out, preferably, in solution or suspension in aqueous alcohol (containing 20 to 50% of water) in the presence of 5 to 10% palladium on charcoal (used in the proportion of 5 to 10% of the weight of the product employed). Mostly operation is at hydrogen pressure comprised between 1 and 50 bars, and temperatures situated between 20° and 40° C.

When hydrogenation is terminated, the solution is filtered to separate the catalyst, when it is concentrated to dryness under vacuum. The residue, generally viscous, is taken up again by suitable solvent, to lead to crystallisation of the salt (II), which is purified by re-crystallisation.

aqueous solution of one of the above-described salts, by means of an alkali carbonate or of a weak base such as ammonia.

The raw materials necessary for the preparation of the compound according to the invention are obtained as described below:

1. 3-amino-1-[1-benzimidazolyl]butane (III)

Benzimidazole (VIII) (1 mole), condensed with methylvinylketone in slight excess (1-1.1 mole), in the presence of a catalytic amount of Triton B (benzyltrimethylammonium hydroxide), gives 1-[1-benzimidazolyl]-3-oxo butane (IX). This reaction is conducted in a non-polar neutral solvent, such as an aromatic hydrocarbon (for example toluene) or, preferably, ethyl acetate. The ketone (IX) is converted, by known process, into its oxime ((X). The latter, by catalytic

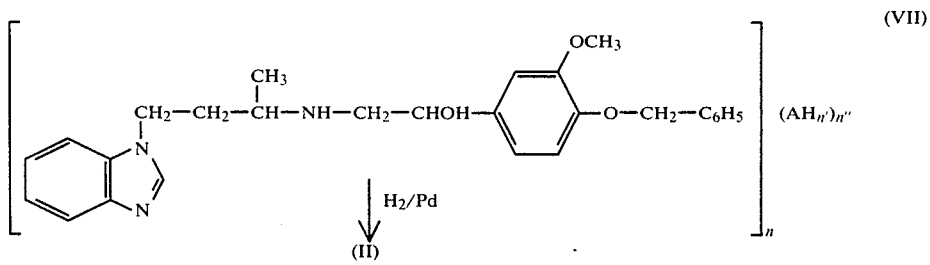

The salts (II), of which the acid residue A is capable of being reduced by catalytic hydrogenation, cannot be obtained by the above-described method. They are prepared, by a known process, by salification of the base (I). The latter is itself obtained, by alkalinisation of the hydrogenation, in an alcoholic medium, in the presence of ammonia and Raney nickel, under pressure (20-80 bars) and heat (50° to 100° C.), results in the amine (III).

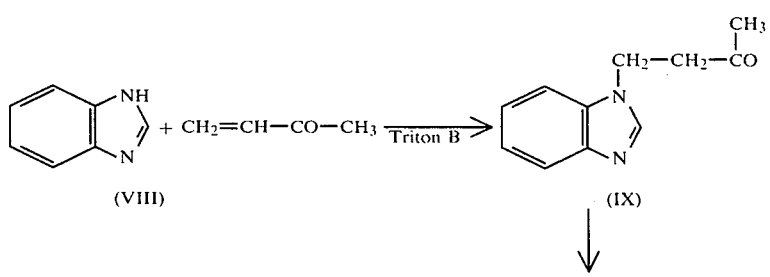

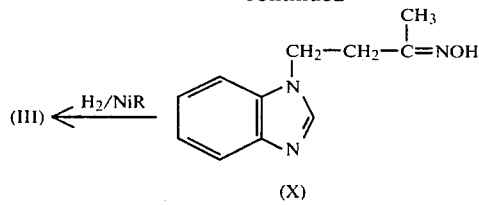

2. (3-methoxy-4-phenylmethoxy)-phenylglyoxal (IVa) and its ethyl acetal[2-ethoxy-2-hydroxy 1-(3-methoxy-4-phenylmethoxy-phenyl)ethanone] (IV$_b$)

These novel compounds are prepared, by known methods, from 1-(3-methoxy 4-phenylmethoxy phenyl)ethanone (XI):

(a) by oxidation, by means of selenium oxide, at 100° C., in a suitable cosolvent, preferably dioxane, the ketone (XI) results directly in the glyoxal (IV$_a$), which, in air, gives a hemihydrate.

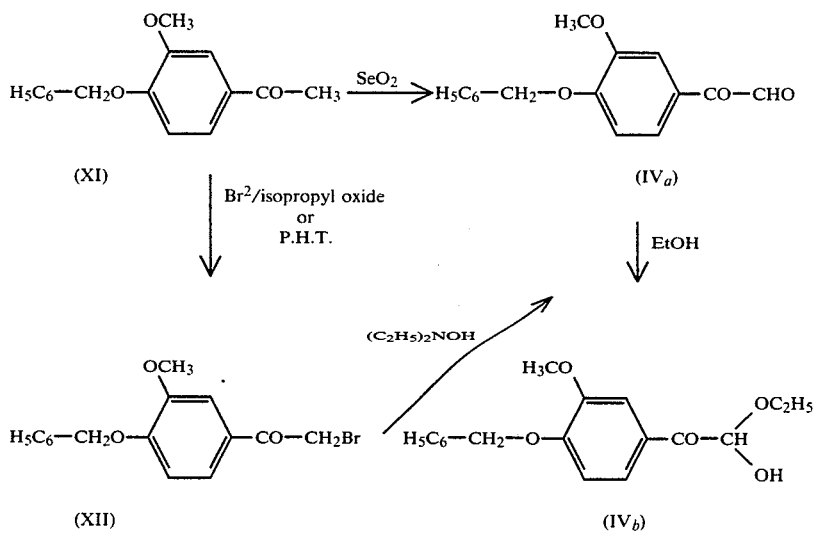

(b) the ketone (XI), treated with bromine, in the presence of a lower alkyl oxide, or better, by 2-pyrrolidone hydrotribromide (P.H.T.) in a chlorinated fatty hydrocarbon (for example chloroform), provides the bromoketone (XII). The latter, by the action of NN-diethylhydroxylamine, by the konwn process [V. E. GUNN and J. P. ANSELME J. Org. Chem. 1977, 42, 754–755] gives the glyoxal (IV$_a$), which, treated with ethanol, provides the hemiacetal (IV$_b$) more easily purifiable than the glyoxal itself or its hemihydrate.

The compound according to the invention and its salts have properties characteristic of "in vitro" and "in vivo" $\beta$-mimetic substances:

Relaxation of the trachea and of the isolated uterus, positive chronotropic action on the isolated atrium.

Antagonism of histaminic bronchospasm, uterorelaxant and tachycardic effect in the aroused or unanesthetised animal.

This $\beta$ mimetic specificity is proved by the antagonistic effect of $\beta$-blocking agents.

The pharmacological effects of the products according to the invention, compared with those of a typical substance (Salbutamol-Albuterol Merck Index X-206), are characterised by weaker cardiostimulant effects. Through this fact, the compounds, according to the invention, have a remarkable selectivity with respect to $\beta_2$ type receptors.

By reason of their pharmacological properties, the product according to the invention and its salts may be recognised as therapeutic agents in pneumology and in obstetrics, particularly in the treatment of asthma and in the case of premature labour risks. According to the indications, they can be administered orally, parenterally or rectally. For the treatment of respiratory disorders, they will also be usable in aerosol form.

For treatments by the oral route, administration will be a function of the weight of the patient and of the seriousness of the syndrome to be treated. The total daily dosage will be comprised between 1.5 to 30 mg, divided into 2 or 3 doses.

For this oral administration, the active substance may be presented in one of the forms generally used for this purpose: tablets, capsules, dragees, and syrups. In these forms, the active principle may be alone or associated with various pharmaceutically acceptable inert supports or vehicles. It will also be possible to add various sweetening substances or flavours generally employed for this purpose.

It is also possible in particular to use tablets dosed with 0.5 to 10 mg of active principle and including various excipients such as: sodium citrate or dicalcium phosphate, at the same time as various disintegrating agents such as: starch (particularly tapioca or potato starch), alginic acid, and certain complex silicates, as well as binding agents, such as saccharose, gum arabic or polyvinylpyrrolidone. The tablets can also include lubricating agents generally used to facilitate tableting, such as talc, magnesium stearate or sodium laurylsulphate.

Similar solid compositions may be employed to fill hard or soft gelatine capsules.

In aqueous solutions intended for oral administration, the active principle will be at a concentration comprised between 0.1 and 2 mg/cm$^3$, which, for a measured amount of 5 cm$^3$ represents a dose of 0.5 to 10 mg of product.

In these solutions, the active principle may be associated with various sweetening, flavouring or colouring agents and, if necessary, emulsifying or suspending agents, associated with diluants such as: water, ethanol, propyleneglycol, or these substances in various associations.

The aerosols will be prepared from aqueous solutions of the active principle at a concentration such that, in use, each inhalation corresponds to the administration of 25 to 500 micrograms of product.

For treatment by the parenteral route, the active principle will be administrable either in perfusion (0.5 to 10 mg in 24 hours), or in intravenous injections (0.4 to 8 mg in 24 hours). For this purpose, it will be used in aqueous solutions, at concentrations comprised between 0.02 and 0.4 mg/cm$^3$. The solutions can be facilitated by the addition of solubilising adjuvants, such as N,N-dimethylformamide, propyleneglycol or lactamide. They will be rendered isotonic, by the addition of a suitable proportion of sodium chloride or glucose.

The final preparations will be passed over a suitable bacterial filter, such as a sintered glass filter or a filter lined with infusorial earth or a filter of unglazed porcelaine. Among the recognized preferred filters, may be mentioned Berkefeld, Chemberland and Seitz filters, where the fluid is aspirated through the filtering wall to drop into a sterile receiver.

For rectal administration, suppositories will be used containing from 0.25 to 5 mg of active compound per unit. The excipients can be: natural or hardened oils, waxes, greases, semi-synthetic glycerides.

The following non-limiting examples are given to illustrate the present invention.

EXAMPLE 1

1-[1-benzimidazolyl]-N-[2-(4-hydroxy-3-methoxyphenyl)2-hydroxy-ethyl]3-amino butane basic sulphate, dihydrate [II, A=SO$_4$, n=2, n'=2, n''=1]

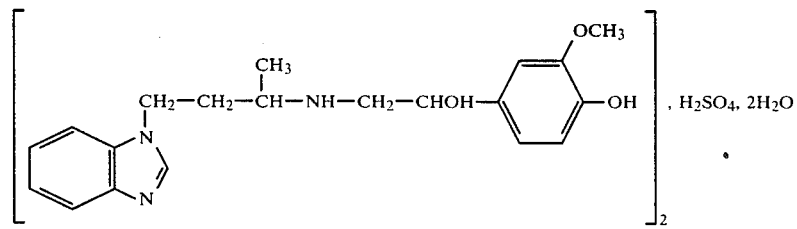

1.

1-[1-benzimidazolyl]-N-[2-(3-methoxy-4-phenylmethoxyphenyl)-2-hydroxy-ethyl]3-amino butane basic sulphate (VII, A=SO$_4$, n=2, n''=2, n'''=1)

In a 1 liter flask, provided with a stirrer, 32.2 g (0.17 mole) of 1-[1-benzimidazolyl]-3-amino butane are dissolved in 400 cm$^3$ of ethanol, and 54 g (0.17 mole) of 2-ethoxy-2-hydroxy-(3-methoxy-4-phenylmethoxyphenyl)-1-ethanone are added thereto. The mixture was stirred for 3 h at ordinary temperature; at the end of the first hour, the hemiacetal passed completely into solution.

The mixture is cooled to 10° C. and there is addded, in small fractions, with good stirring, 12.9 g (0.34 mole of fine powdered sodium borohydride. The solution is stirred a further 3 h, then left overnight at room temperature.

The solution is made acid by the addition of 45 cm$^3$ of methanesulphonic acid, then diluted with 250 cm$^3$ of water, to dissolve the inorganic salts which have precipitated. The mixture is stirred 1 h at room temperature.

The greater part of the ethanol is removed, by concentration under vacuum of the solution to about ⅓rd of its volume. To the residue is added 400 cm$^3$ of water. The solution is extracted with ethyl acetate (6×100 cm$^3$) in order to remove a slight insoluble material.

The aqueous phase is made alkaline by the addition of caustic soda. The base which precipitates is extracted with ethyl acetate (200 cm$^3$, then 3×100 cm$^3$). The extracts, combined, were washed with water (2×100 cm$^3$), dried (MgSO$_4$), filtered and evaporated to dryness under vacuum, at 100° C.

74 g of a viscous oil is obtained which is dissolved in 180 cm$^3$ of ethanol. The solution is stirred 1 h with 35 g of Raney Ni. This operation is for the purpose of removing possible catalyst poisons used in the following operations.

The solution is filtered and the Raney Nickel washed with ethanol (2×25 cm$^3$). The combined filtrates were concentrated under vacuum, to a volume of 100 to 150 cm$^3$, then brought back to an exactly measured volume, (250 cm$^3$), by the addition of the necessary amount of ethanol. In this way solution (A) is obtained.

On 0.5 cm$^3$ of this solution, determination of the basicity in anhydrous medium (acetic acid) followed, with N/10 perchloric acid (in the example described, 5.8 cm$^3$ of ClO$_4$H 0.102N were required). From the result thus obtained, the total amount of sulphuric acid necessary for the salification of half of the basic functions of the 1-[1-benzimidazolyl]-N-[2-(3-methoxy-4-phenylmethoxy-phenyl)-2-hydroxy-ethyl]3-amino butane present in the solution (A) was calculated. In the example cited, this calculation came to 7.3 g of H$_2$SO$_4$.

This weight of sulphuric acid was added, with cooling, in one third of its weight of water (5 cm$^3$), and then to the mixture was added the same volume of cold ethanol (5 cm$^3$).

The solution so obtained was added, slowly, with stirring, to the mother liquor (A). The formation of a precipitate was observed transiently which repassed into solution. The latter was heated under reflux until the beginning of the appearance of crystals, then left for 24 h at ordinary temperature.

The precipitate was drained and resuspended in 570 cm³ of acetone. The mixture was stirred and heated under reflux for 1 h. The solid was drained, washed with acetone and dried. 54.9 g of crude product was obtained, sufficiently pure for the following operation, MP~178°-180° C. (pasty).

For the analysis, 1 g of this salt was recrystallised in 10 cm³ of methylcellosolve, MP~184°-185° C. (pasty melt).

Analysis for C₅₄H₆₄N₆O₁₀S (M.W. 989.16): Calculated %: C, 65.56; H, 6.52; N, 8.50; S, 3,24. Found %: C, 65.43; H, 6.75; N, 8.75; S, 3.38.

N.M.R. spectrum * (D.M.S.O.d₆)δ=8.15 ppm, 1H

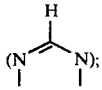

δ 6.5 to 8 ppm, m, 13H (aromatics); δ=4.95 ppm, s, 2H (—O—CH₂—); δ=4.65 ppm, m,

1H(—CH—);
      |
      OH

δ=4.25 ppm, t,

2H(—N—CH₂—),
      \\
      —N

J=7 Hz; δ=3.7 ppm, s, 3H(—OCH₃); δ=2.8 ppm, m, 3H(—CH—NH—CH₂—); δ=2.0 ppm, m,

2H(—CH₂—CH—);
            |

δ=1.1 ppm, d, 3H(—CH₃), J=6.5 Hz.
*The N.M.R. spectra was obtained on the BRUKER 80 MHz equipment.

2. Hydrogenation 49.5 g (0.05 mole) of the sulphate described above were suspended in 730 cm³ of 50% ethanol and stirred, in a hydrogen atmosphere, at ordinary pressure, at 40° C., in the presence of 5 g of 10% palladium on charcoal. The absorption was terminated in 3 h. After returning to room temperature, the catalyst was separated by filtration and washed with ethanol (2×50 cm³). The solution was concentrated to dryness on a Rotavapor.

The viscous residue was taken up again, with stirring, with 400 cm³ of 90% ethanol. After dissolution, the salt started to precipitate; the crystallization was left to develop at room temperature overnight.

The solid (33.1 g) was drained and dried in a phosphoric vacuum. It was recrystallised, in a nitrogen atmosphere, in 140 cm³ of water. It was drained and dried in the phosphoric vacuum, then restored to air (moisture take-up), until constant weight. 20.6 g of dihydrate, MP 150° C. was obtained.

Analysis for C₄₀H₅₀N₆O₆. H₂SO₄, 2H₂O (M.W. 844.96): Calcul. %: C, 56.85; H, 6.68; N, 9.95; S, 23.79. Found %: C, 56.67; H, 6.74; N, 10.20; S, 3.76.

N.M.R. spectrum (D₂O): δ=8.25 ppm,

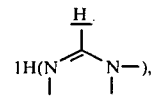

7.87 to 7.25 ppm, m, 4H (aromatic); δ=7.1 to 6.75 ppm, m, 3H (aromatics); δ=4.80 ppm, m,

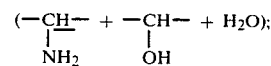

δ=4.37 ppm, m, 2H

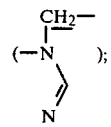

δ=3.88 ppm, s, 3H (—OCH₃); δ=3.15 ppm, d, 2H(NH—CH₂—CHOH), J=6 Hz; δ=2.25 ppm, m, 2H

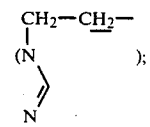

δ=1.50 ppm, d, 3H

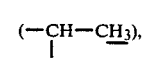

J=7 Hz.

The raw materials necessary for the preparation of the compounds of example 1 were obtained as described below:

(a) 3-amino-1-[1-benzimidazolyl]butane

In a 2 liter flask, with 3 necks, provided with a stirrer, a reflux coolant, a dropping funnel and a thermometer were stirred a suspension of 118 g (1 mole) of benzimidazole in 450 cm³ of ethyl acetate. 2 cm³ of a 40% solution of triton B in methanol was added, then 79 g (92 cm³=1.1 mole) of freshly distilled methylvinylketone.

The mixture was brought to 40° C., at which temperature the reaction started with the release of heat. Heating was stopped, the temperature rose to 70° C.; when it had returned to 40° C., it was kept for 1 h. The mixture was then stirred at 20° C. for 3 h.

The viscous brown solution was diluted with 150 cm³ of ethyl acetate, then stirred 30 min. with 20 g of vegetable charcoal. It was filtered, washed by decantation, with water (3×150 cm³), then dried (Na₂SO₄) and filtered.

The solvent was evaporated under vacuum, the viscous residue was stirred with 250 cm³ of isopropyl oxide. The crystals were drained and dried (Yield: 166 g). They were recrystallised in 800 cm³ of a mixture of ethyl acetate (1 volume)-isopropyl oxide (1 volume). 121 g (64%) of 1-[1-benzimidazolyl]-3-oxo butane (IX), PM. 64° C., was obtained.

Analysis for $C_{11}H_{12}N_2O$ (188.22): Calcul. %: C, 70.18; H, 6.42; N, 14.88. Found %: C, 69.97; H, 6.62; N, 14.88.

260 g (1.38 mole) of this ketone, in a solution 900 cm³ of ethanol were stirred in a 5 liter flask provided with a reflux coolant.

A solution of hydroxylamine acetate was added which had been prepared from 191.8 g (2.76 moles) of hydroxylamine hydrochloride, 900 cm³ of water and 375 g (2.75 moles) of sodium acetate(trihydrate).

The mixture was stirred and heated 2 h under reflux. After returning to ordinary temperature, the oxime crystallized. It was drained, washed with water then washed with ethanol and dried in air. 214 g (Yield 77%) was obtained of 1-[1-benzimidazolyl]-3-oximino butane (X), MP.=144°-146° C., after recrystallisation in 50% ethanol. MP. 148°-150° C.

Analysis for $C_{11}H_{13}N_3O$ (M.W. 203.24): Calcul. %: C, 65.00; H, 6.45; N, 20.68. Found %: C, 64.90; H, 6.15; N, 20.91.

In an autoclave of 1 liter, 107 g (0.53 mole) of oxime were suspended in 300 cm³ of ethanol; 50 cm³ of 34% ammonia solution and 35 g of Raney nickel were added. The mixture was stirred in a hydrogen atmosphere, under an initial pressure of 80 bars, at 70°-80° C. After 5 hours, the operation was ended. The catalyst was separated by filtration. The solution was concentrated to dryness under vacuum; the viscous residue was taken up again with 150 cm³ of water and 80 cm³ of caustic soda. The base which separates was extracted with chloroform (3×150 cm³). The organic solution was dried (MgSO₄). The solvent was evaporated and the residue was fractionated under vacuum.

76.7 g (Yield 77%) of 3-amino-1-[1-benzimidazolyl]-butane, was obtained, $E_{0.7}$: 164°-168° C., hygroscopic.

N.M.R. spectrum. (CDCl₃)—δ=7.35 ppm, m, 2H and δ=6.85 ppm, m,

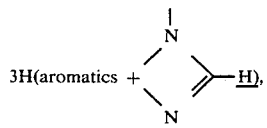

3H(aromatics + ... —H),

δ=4.0 ppm, t,

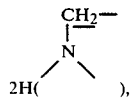

2H( ),

J=7 Hz; δ=2.66 ppm, m, 1H

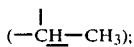

(—CH—CH₃);

δ=1.70 ppm, m, 2H

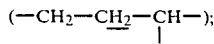

(—CH₂—CH₂—CH—);

δ=1 ppm, 5H (—CH₃+NH₂), 2H, removable by D₂O.

(b) 2-ethoxy-2-hydroxy-1-(3-methoxy-4-phenylmethoxy-phenyl)-ethanone 79.4 g (0.237 mole) of 2-bromo 1-(3-methoxy-4-phenylmethoxy-phenyl)-ethanone and 21.1 g (0.237) of diethylhydroxylamine in 610 cm³ of methanol were stirred and heated under reflux for 8 h.

The bromoketone passed into solution during the first hour.

The methanol was driven off under vacuum, and the residue was taken up again with 500 cm³ of toluene.

The insoluble diethylamine hydrobromide was separated by filtration.

The toluene solution was washed with water until the aqueous extracts no longer contained Br⁻ ions. After drying (MgSO₄), the organic solution was concentrated to dryness under vacuum. The residue, red in colour, was dissolved in 140 cm³ of ethanol and the solution was left for 24 h at ordinary temperature. The solid which had crystallized was drained and recrystallized in 160 cm³ of ethanol.

53 g (Yield 71%) of hemiacetal were obtained, MP. 98°-100° C.

Analysis for $C_{18}H_{20}O_5$ (M.W. 316.34): Calcul. %: C, 68.34; H, 6.37. Found %: C, 68.57; H, 6.56.

N.M.R. spectrum (D.M.S.O.d₆):

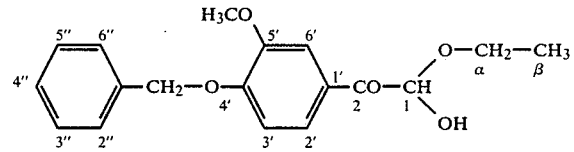

δ=7.25 ppm; d (split), 1H (H₂'); δ=7.10 ppm, d, 1H (H₆') J (H₂'–H₆')=2 Hz; δ=6.95 ppm, m 5H (aromatics: 2″+3″+4″+5″+6″); δ=6.7 ppm, d, 1H (H₃'), J(H₂'–H₃')=8 Hz; δ=6.30 ppm, d, 1H (exchangable with D₂O) (OH); δ=5.12 ppm, d, 1H (H₁), J(O-H—H₁)=8 Hz; δ=4.82 ppm, s, 2H (—CH₂O); δ=3.57 ppm, s, 3H (—CH₃O); δ=3.5 ppm, q, 2H (—CH₂); δ=1.05 ppm, t (—CH₃β) J [CH₂α—CH₃β]=7 Hz.

EXAMPLE 2

1-[1-benzimidazolyl]-N-[2-(4-hydroxy-3-methoxy-phenyl)-2-hydroxy-ethyl]-3-amino-butane dihydrochloride, dihydrate (II, A=Cl, n=1, n'=1, n″=2)

(a) The operational method described in Example 1 was followed; 38 g (0.2 mole) of 3-amino-1-[1-benzimidazolyl]butane, in solution in 550 cm³ of ethanol, were supplemented with 56 g of (3-methoxy-4-phenylmethoxy)phenylglyoxal(hemihydrate), and the mixture was stirred for 3 h at ordinary temperature.

The solution was cooled to 10° C., then 15.2 g (0.4 mole) of sodium borohydride was added thereto. When the reduction was finished, the medium was acidified with 40 cm³ of methanesulphonic acid. After stirring for 1 h at ordinary temperature, 100 cm³ of water was added and it was concentrated under vacuum to ⅓rd of the volume; the residue was taken up again with 300 cm³ of water. After extraction with ethyl acetate, the solution was made alkaline by the addition of caustic soda; the base was extracted with ethyl acetate (200 cm³+100 cm³+100 cm³). After drying (MgSO₄) and concentration under vacuum, 89 g of crude base were obtained.

It was dissolved in 150 cm³ of ethanol and stirred for 1 h with 35 g of Raney nickel. The solution was filtered, heated to 70° C., and 49 cm³ of 8.15N alcoholic hydrochloric acid was added with stirring. A precipitate formed initially passed into solution, at the end of the addition. After returning to ordinary temperature (start of crystallisation), the mixture was left overnight in a refrigerator. The crystals were drained, washed with ethanol, then with acetone and dried under phosphoric vacuum.

In this way 56 g of a monohydrate of 1-[1-benzimidazolyl]-N-[2-(3-methoxy-4-phenylmethoxy-phenyl)-2-hydroxy-ethyl]-3-amino butane dihydrochloride was obtained. MP. ~190° C. (pasty).

Analysis for $C_{27}H_{31}O_3N_3$, 2 HCl, $H_2O$ (M.W. 536.49): Calcul. %: C, 60.44; H, 6.58; N, 7.83; Cl, 13.22. Found %: C, 60.95; H, 6.34; N, 7.94; Cl, 13.26.

(b) Procedure was as described in example 1; 20 g of this dihydrochloride, in suspension in 250 cm³ of 50% ethanol were hydrogenated under pressure (20 bars), in the presence of 2 g of 10% palladium on charcoal, at ordinary temperature.

After filtration, the solution was concentrated to dryness in the Rotavapor, the residue was taken up again with 150 cm³ of ethanol, and concentrated again to dryness. The viscous residue was dissolved in 95 cm³ of 95% ethanol. The solution was stirred until the start of crystallization. After standing 24 h at ordinary temperature, the salt was drained then recrystallized in 56 cm³ of ethanol. It was dried overnight in a phosphoric vacuum, then left in air until constant weight (moisture take-up). 10.8 g of a hydrate solvated by one molecule of ethanol was obtained.

Analysis for $C_{20}H_{25}N_3O_3$, 2HCl, $H_2O$, $C_2H_5OH$ (M.W. 492.44): Calcul. %: C, 53.66; H, 7.16; N, 8.53; Cl, 14.40. Found %: C, 53.49; H, 7.22; N, 8.85; Cl, 14.24.

The presence of solvation alcohol was confirmed by the N.M.R. spectrum.

N.M.R. spectrum ($D_2O$): δ=9.25 ppm, s,

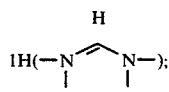

δ=6,7 to 8 ppm, m, 7H (aromatics); δ=4.95 ppm, t, 1H,

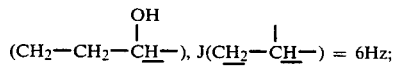

δ=4.7 ppm, m,

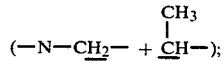

δ=3.82 ppm, s, 3H (—OCH₃); δ=3.67 ppm, q, 2H (CH₃—CH₂—OH), J=7 Hz; δ=3.3 ppm, d, 2H (NH—C$\underline{H}_2$—); δ=2.5 ppm, q, 2H

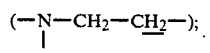

δ=1.55 ppm, d, 3H,

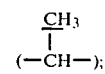

δ=1.22 ppm, t, 3H, (C$\underline{H}_3$—CH₂OH), J=7 Hz.

The hemihydrate of (3-methoxy-4-phenylmethoxy)-phenylglyoxal, necessary for this preparation, was obtained as described below:

44.4 g of selenious anhydride (0.4 mole), 350 cm³ of dioxane and 10 cm³ of water was stirred and heated under reflux until dissolution of the selenium dioxide.

After returning to 80° C., 102.5 g (0.4 mole) of 1-(3-methoxy-4-phenylmethoxy)-ethanone were added, and the mixture was stirred and heated under reflux until complete disappearance of the starting ketone (established by T.L.C. on silica gel, F. 257 MERCK; eluent: chloroform: 95 volumes, methanol: 5 volumes), which required from 8 to 10 h.

After cooling, the selenium formed was separated by filtration, the solution was concentrated to dryness under vacuum. The residue was dissolved in 150 cm³ of toluene and 100 cm³ of water were added, with stirring. The hemihydrate crystallized slowly. After standing one night, at ordinary temperature, it was drained, then dissolved under reflux in 150 cm³ of toluene supplemented with 20 cm³ of water. The hot solution was filtered on cellite (elimination of selenium particles). The crystals which precipitated by cooling were drained and dried in air. 90.4 g of a hemihydrate were obtained MP. indistinct ~140° C.

Analysis for $C_{16}H_{14}O_4$, 0.5 $H_2O$ (M.W. 279.27): Calcul. %: C, 68.81; H, 5.41. Found %: C, 68.80; H, 5.59; C, 68.85; H, 5.63.

EXAMPLE 3

1-[1-benzimidazolyl]-N-[2-(4-hydroxy-3-methoxy-phenyl)-2-hydroxy-ethyl]-3-amino butane-neutral sulphate, monohydrate (II, A=SO₄, n=1, n'=2, n''=1)

16.5 g of crude 1-[1-benzimidazolyl]-N-[2-(3-methoxy-4-phenyl-methoxy-phenyl)-2-hydroxy ethyl]-3-amino butane, obtained according to example 1, was dissolved in acetic acid, and the volume brought back to 100 cm³. 1 cm³ of solution was taken off and the basicity was determined by 0.105N perchloric acid. From this result, the amount of 2N sulphuric acid (in acetic solution) necessary to neutralize the whole of the bases was calculated (namely 31.5 cm³, for the example cited). This volume of reagent was added to the base solution, the solvent was driven off by evaporation in a Rotavapor, the residue was taken up again in 50 cm³ of water which were evaporated in the same apparatus. This operation was repeated again, in order to remove the acetic acid as completely as possible. The residue was taken up again with 75 cm³ of water and left at ambiant temperature for 24 h. The salt which crystallized was drained, washed with iced water and dried in a phosphoric vacuum. 15.8 g of 1-[1-benzimidazolyl]-N-[2-benzimidazolyl]-N-[2-(3-methoxy-4-phenylmethoxy-phenyl)-2-hydroxy-ethyl]-3-amino butane neutral sulphate was obtained, MP 170°–180° C.

Analysis for $C_{27}H_{31}N_3O_3$, $H_2SO_4$ (M.W. 543.56): Calcul. %: C, 59.66; H, 6.12; N, 7.73. Found %: C, 59.40; H, 6.39; N, 7.85.

15.7 g of this sulphate, in suspension in 250 cm³ of 50% ethanol were hydrogenated in the presence of 1.6 g of 10% Pd on charcoal, as described in example 1, at 40° C., at ordinary pressure for a period of 4 h. After filtration, the solution was concentrated to dryness in a Rotavapor, the residue was taken up again with 100 cm³ of ethanol and concentrated again. This evaporation was repeated, to remove the maximum of water. The residue was taken up again with 100 cm³ of ethanol and left for 28 h at ordinary temperature. The salt which crystallized was drained and dried (13 g). It was recrystallized in 80 cm³ of 70% ethanol. After draining, drying under a phosphoric vacuum and moisture take-up in air, 8.5 g of 1-[1-benzimidazolyl]-N-[2-(4-hydroxy-3-methoxy-phenyl)-2-hydroxy-ethyl]-3-amino butane, neutral suphate, monhydrate solvated with ½ molecule of ethanol, was obtained.

Analysis for $C_{20}H_{25}N_3O_3$, $H_2O$, $H_2SO_4$, 0.5 $C_2H_5OH$ (M.W. 494.55): Calcul. %: C, 50.99; H, 6.52; N, 8.50; S, 6.48. Found %: C, 50.90; H, 6.38; N, 8.43; S, 6.54.

The presence of the half-molecule of ethanol is confirmed by the N.M.R. spectrum.

EXAMPLE 4

1-[1-benzimidazolyl]-N-[2-(4-hydroxy-3-methoxy-phenyl)-2-hydroxy-ethyl]-3-amino butane furmarate (1)
1-[1-benzimidazolyl]-N-[2-(4-hydroxy-3-methoxy-phenyl)-2-hydroxy-ethyl]-3-amino butane 2 g of the hydrated and solvated dihydrochloride, prepared according to example 2, were dissolved in 10 cm³, of water; the solution was made alkaline by the addition of 10 cm³ of a saturated sodium carbonate solution. The viscous base which precipitated was extracted with dichloromethane (20 cm³+3×15 cm³). The organic phases, combined, were dried ($MgSO_4$), and the solvent was evaporated under vacuum.

The 1-[1-benzimidazolyl]-N-[2-(4-hydroxy-3-methoxy-phenyl)-2-hydroxy-ethyl]-3-amino butane so obtained was a viscous oil whose N.M.R. spectrum confirmed the announced structure:

N.M.R. spectrum(C.D.Cl₃): δ=7.75 ppm, s,

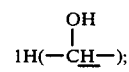

δ=7.75 a 7.6 ppm, m, 1 H arom.; δ=7.35 to 7.1 ppm, m,

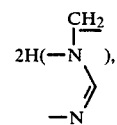

δ=6.9 to 6,7 ppm, m,

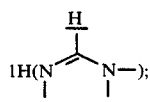

δ=4.55 ppm, m,

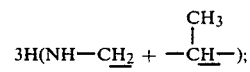

δ=4.15 ppm, t,

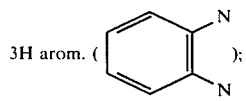

J=7 Hz; δ=3.92 ppm, m, 3H (2 OH+NH); δ=3.75 ppm, s, 3H (—OCH₃); δ=2,3 to 2.9 ppm, m,

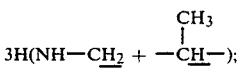

δ=1.80 ppm, q,

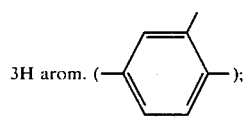

J=7 Hz; δ=1.02 ppm, d,

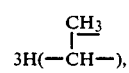

J=6.5 Hz.

(2) Fumarate salt

The residue (1.3 g) was dissolved in 10 cm³ of ethanol; 0.46 g of fumaric acid were added. The suspension was heated under reflux until dissolution. By cooling, the salt crystallized. It was drained and recrystallized in 10 cm³ of 90% ethanol. 1.2 g were obtained (Yield 69.5%) of the salt, MP. 200° C.

Analysis for $C_{20}H_{25}N_3O_3$, HOOCCH=CH—COOH (P.W. 471.50): Calcul. %: C, 61.13; H, 6.20; N, 8.91. Found %: C, 60.78; H, 6.81; N, 8.73.

The compounds according to the invention were the subject of pharmacological study in the principal fields of activity of β-mimetic agents.

The study was carried out in particular with the compound of Example 1 and that of Example 2.

In the presentation of the experiments and of the results, the compound of Example 1 is called: compound A and the compound of Example 2 is called: compound B.

These two compounds were the subject of an acute toxicity study in the mouse.

Intraveneously, the compound A has an $LD_{50}$ of 114 mg/kg (confidence limits, at p=0.05: 102–128) namely, expressed as base: 96 mg/kg (85–107); the compound B had an $LD_{50}$ of 148 mg/kg (confidence limits, at p=0.05: 130–168) namely, expressed as base: 106 mg/kg (94–121).

The two compounds had similar toxicity and the pharmacological study was able, indifferently, to be carried out with one or the other, the results being, in the two cases, expressed by weight of base per kg of body weight for the in vivo tests and in molar concentration for the in vitro tests.

The pharmacological study was carried out comparatively with Salbutamol (sulphate) which is a β-adrenergic stimulant and a bronchodilater commercially available, for which the results have been expressed in the same way as weight of base per kg of body weight or in molar concentration.

1. RELAXANT ACTIVITY ON THE TRACHEA OR BRONCHI

1.1 Relaxant activity of the tracheal muscle in vitro

This activity was studied on an isolated trachea preparation of the guinea pig (chain of tracheal rings, according to CASTILLO and BEER. Journ. Pharmacol. Exp. Ther. 1947 90 104–109), kept alive in a KREBS solution. The effect of cumulative doses on the pressure of the preparation was recorded.

The activity of the substance was expressed by the value of the molar $CD_{50}$ (decontracting concentration 50=concentration giving 50% of maximum relaxation), of which the negative log. is the value $pD_2$, and by the intrinsic activity corresponding to maximum effect.

These values were determined in parallel for the compound A and Salbutamol, on 6 preparations for each.

|  | COMPOUND A | SALBUTAMOL |
|---|---|---|
| CD 50 | $7.1 \times 10^{-8}$ mol | $1.5 \times 10^{-8}$ mol |
| $pD_2$ | 7.15 | 7.82 |
| Maximum response (decontraction) | 390 mg | 358 mg |
| Intrinsic activity | 1.09 | 1.00 |

The activity of the compound A on the tracheal muscle is very close to that of Salbutamol.

1.2 Bronchodilator activity, in vivo 1.2.1 In the anesthesized guinea pig (method of KONZETT. Arch. Exp. Pathol. Pharmakol. 1940 195 71-74)

A bronchospasm was caused by intravenous histamine injection. The bronchodilator activity was shown by partial or total inhibition of this spasm.

The product studied was administered intravenously or intraduodenaly and histamine injected then at different times to follow the delay in appearance and the duration of the inhibiting effect of the treatment.

1.2.1.1. Intravenous treatment

The results below are the averages of the values obtained in 10 animals.

| Dose | COMPOUND A % inhibition in time (min.) | | | | | | |
|---|---|---|---|---|---|---|---|
| μg base/kg | 1 | 5 | 10 | 15 | 30 | 45 | 60 |
| 0.08 | 1 | 1 | 0 | 0 | | | |
| 0.25 | 9 | 1 | 0 | 0 | | | |
| 0.8 | 36 | 3 | 2 | 3 | | | |
| 2.5 | 66 | 13 | 8 | 8 | | | |
| 8 | 73 | 17 | 12 | 8 | | | |
| 25 | 92 | 52 | 38 | 28 | | | |
| 84 | 92 | 80 | 70 | 63 | 51 | 36 | 21 |

| Dose | SALBUTAMOL % inhibition in time (min.) | | | | | | |
|---|---|---|---|---|---|---|---|
| μg base/kg | 1 | 5 | 10 | 15 | 30 | 45 | 60 |
| 0.08 | 8 | 2 | 0 | 1 | | | |
| 0.25 | 25 | 6 | 2 | 2 | | | |
| 0.8 | 54 | 8 | 7 | 2 | | | |
| 2.5 | 75 | 13 | 8 | 4 | | | |
| 8 | 91 | 35 | 13 | 8 | | | |
| 25 | 97 | 78 | 34 | 22 | | | |
| 83 | 94 | 81 | 60 | 55 | 50 (n = 9) | 30 | 17 (n = 9) |

Intravenously, the compound A and Salbutamol have an activity of the same order, although very slightly less for compound A at low doses; at the highest dose, the effect is intense and lasting, the compound A had an activity at least equal to that of Salbutamol.

1.2.1.2. Intraduodenal treatment

The results below are the averages of the values obtained in 10 animals.

| Dose | COMPOUND A % inhibition in time (min.) | | | | | | | |
|---|---|---|---|---|---|---|---|---|
| mg base/kg | 1 | 5 | 15 | 30 | 45 | 60 | 90 | 120 |
| 0.25 | 11 | 27 | 26 | 26 | 19 | 13 | 9 | — |
| 0.8 | 16 | 60 | 61 | 44 | 29 | 23 | 21 | — |
| 2.5 | 20 | 73 | 65 | 53 | 44 | 39 | 34 | 30 |
| 8 | 51 | 82 | 82 | 71 | 67 | 65 | 59 | 55 (n = 9) |

| Dose | SALBUTAMOL % inhibition in time (min.) | | | | | | | |
|---|---|---|---|---|---|---|---|---|
| mg base/kg | 1 | 5 | 15 | 30 | 45 | 60 | 90 | 120 |
| 0.8 | 4 | 18 | 16 | 16 | 13 | 13 | — | — |
| 2.5 | 2 | 14 | 32 | 34 | 29 | 23 | 15 | 10 |
| 8 | 31 | 64 | 76 | 72 | 65 | 58 | 52 | 37 (n = 8) |

The threshold active dose of the compound A is situated at 0.25 mg/kg; the effect becomes intense between 0.8 and 2.5 mg/kg and more lasting at 8 mg/kg.

Salbutamol has a threshold dose comprised between 0.8 and 2.5 mg/kg (closest to 2.5); it must reach 8 mg/kg to obtain a high activity, comprised between those shown respectively by 2.5 and 8 mg/kg of compound A.

By this route, the compound A is more active than Salbutamol.

1.2.2. In the anesthesized dog (recording of the intratracheal pressure)

A bronchospasm was caused by intravenous injection and histamine. The bronchodilator activity was shown by partial or total inhibition of this spasm.

The products studied were administered intraduodenally and the histamine injected then at various times to follow the effect of the treatment.

The results borne in the table below are the averages of the values obtained in 3 animals for each product.

| Dose | COMPOUND A % inhibition in time (min.) | | | | |
|---|---|---|---|---|---|
| mg base/kg | 5 | 20 | 35 | 60 | 90 |
| 0.025 | 48 | 60 | 67 | 63 | 62 |

-continued

| Dose | COMPOUND A % inhibition in time (min.) | | | | |
|---|---|---|---|---|---|
| mg base/kg | 5 | 20 | 35 | 60 | 90 |
| 0.08 | 70 | 78 | 76 | 70 | 60 |

| Dose | SALBUTAMOL % inhibition in time (min.) | | | | |
|---|---|---|---|---|---|
| mg base/kg | 5 | 20 | 35 | 60 | 90 |
| 0.025 | 21 | 65 | 63 | 61 | 65 |
| 0.08 | 8 | 50 | 56 | 55 | 52 |

The two products had an activity equivalent to 0.025 mg/kg but the compound A acted more rapidly (inhibition already strong in 5 minutes).

At the dose of 0.08 mg/kg, the compound A, whose activity was higher than or equal to that of Salbutamol, is characterised by its great speed of action.

2. UTERUS RELAXING ACTIVITY

2.1. In vitro

This activity was investigated on a rat uterus preparation, put into estrus by cutaneous injection of oestradiol benzoate. The uterine horns were kept alive in a RINGER-LOCKE solution, modified by GADDUM and VOGT.

The relaxant effect of compound A and of Salbutamol was studied with respect to the contractions caused by acetyl-choline or serotonine, by the prior addition of isolated increasing concentrations; these compounds had an inhibiting effect proportional to the concentration used.

Their activity is expressed by the value of the molar $CE_{50}$ (effective concentration 50, inhibiting by 50% the control contraction induced by the contracting agent).

Each $CE_{50}$ indicated below was obtained from the results of 7 preparations.

| Contracting Agent | $CE_{50}$ mol | |
|---|---|---|
| | Compound A | Salbutamol |
| Acetylcholine | $6.7 \times 10^{-10}$ | $5.0 \times 10^{-9}$ |
| Serotonine | $2.4 \times 10^{-9}$ | $8.3 \times 10^{-9}$ |

The activity of the compound A on the uterus is of the same order of that of Salbutamol.

2.2. In vivo

The test was carried out also in the rat.

The aminal was anesthesied by ethyl carbamate.

The contractions caused in an exposed uterine horn immersed in a nutrient bath were recorded (bath: RINGER-LOCKE modified by GADDUM and VOGT). These contractions were induced by the intravenous injection of ocytocine, at the dose of 0.1 IU per kg.

After a control recording of the effects of the latter, the compound A or the Salbutamol were administered intravenously and the further ocytocine injection was carried out; its effect was compared with that of the control reaction.

Compound A, administered at the dose of 16.8 μg/kg had an inhibiting activity comparable with that of salbutamol, administered at the dose of 24.9 μg/kg.

3. CARDIOVASCULAR ACTIVITY

3.1. Activity on the heart rate, in vitro

This action was studied on an isolated right atrium preparation of the guinea pig kept alive in a RINGER solution. The effect of cumulative doses on the heart rate was recorded. The results below are the averages of 6 preparations of the compound A, of 4 for Salbutamol

| Product | Concentration mol | Heart rate (beats per min.) | | |
|---|---|---|---|---|
| | | basal | maximum | Increase |
| Compound A | $1 \times 10^{-7}$ | 209 | 249 | +40 |
| | $1 \times 10^{-6}$ | 209 | 258 | +49 (maxi) |
| | $1 \times 10^{-5}$ | 209 | 256 | +47 |
| Salbutamol | $1 \times 10^{-8}$ | 202 | 251 | +49 |
| | $1 \times 10^{-7}$ | 202 | 292 | +90 |
| | $1 \times 10^{-6}$ | 202 | 308 | +106 |
| | $1 \times 10^{-5}$ | 202 | 317 | +115 (maxi) |
| | $1 \times 10^{-4}$ | 202 | 312 | +110 |

Compound A increases the rate but the maximum effect is very much less than that of Salbutamol; this low activity prevents calculation of a $CE_{50}$ and a $pD_2$ for the compound A (maximum less than 50% of the maximum tachycardia obtained with isoprenaline on the same preparation, at the start of the test).

Compound a, whilst having characteristic tachycardiac activity of β-mimetic agents, had only a partial effect, very much less than that of Salbutamol.

3.2. In vivo activity

3.1.1. Activity on the heart rate and on the mean aortic pressure of the anesthetisied dog The activity of the compound A and of Salbutamol was studied on 2 batches of 3 dogs per product: one in spontaneous respiration, the other in artificial respiration; the two substances were administered intraduodenally at 3 doses: 0.008–0.025 and 0.08 mg/kg.

The table below shows the maximum effect obtained on the heart-rate and the average aortic pressure.

| Parameter recording | Type of respiration | Maximum cumulative effect | |
|---|---|---|---|
| | | Compound A | Salbutamol |
| Heart rate | Spontaneous | +17 cpm (15 min after 0.08 mg/kg) | +26 cpm (20 min after 0.08 mg/kg) |
| | Artificial | +20 cpm (10 min after 0.08 mg/kg) | +41 cpm (15 min after 0.025 mg/kg) |
| Average aortic pressure | Spontaneous | −15 mmHg (20 min after 0.08 mg/kg) | −40 mmHg (1 h after 0.08 mg/kg) |
| | Artificial | −26 mmHg (75 min after 0.08 mg/kg) | −36 mmHg (90 min after 0.08 mg/kg) |

Compound A is a little less tachycardiac and hypotensive than Salbutamol.

3.2.2. Action on heart rate on the un-anesthetised dog

The experiment related to 12 Beagle dogs divided into 3 groups of 4; each group was treated orally, with 2 doses of compound B and Salbutamol, with a resting time of several days between the tests.

Each average noted in the table below relates to 12 dogs.

|  | COMPOUND B | | | | SALBUTAMOL | | | |
|---|---|---|---|---|---|---|---|---|
|  | 22 μg base/kg | | 72 μg base/kg | | 25 μg base/kg | | 83 μg base/kg | |
| Times | av. | variat. | av. | variat. | av. | variat. | av. | variat. |
| 0 | 94 | — | 90 | — | 92 | — | 90 | — |
| 15 min | 130 | +36 | 147 | +57 | 142 | +50 | 163 | +73 |
| 30 min | 129 | +35 | 162 | +72 | 165 | +73 | 194 | +104 |
| 1 h | 129 | +35 | 162 | +72 | 170 | +78 | 197 | +107 |
| 2 h | 119 | +25 | 160 | +70 | 156 | +64 | 195 | +105 |
| 3 h | 109 | +15 | 146 | +56 | 137 | +45 | 172 | +82 |
| 4 h | 104 | +10 | 132 | +42 | 130 | +38 | 150 | +60 |
| 5 h | 102 | +8 | 125 | +35 | 120 | +28 | 148 | +58 |
| 6 h |  |  | 115 | +25 |  |  | 141 | +51 |
| 7 h |  |  | 112 | +22 |  |  | 138 | +48 |

The framed values correspond to the maximum effect observed

At an equivalent dose level, Salbutamol is more active than compound B: the effect of the low dose of Salbutamol is equal to that of the high dose of compound B (respectively 25 and 72 μg/kg).

Compound B is hence distinctly less tachycardiac than Salbutamol in the aroused dog.

4. β-STIMULANT SPECIFICITY

The β-stimulant specificity was proved in two fields:
respiratory (guinea pig trachea, in vitro)
cardiovascular (heart rate of the dog, in vivo) by the antagonistic effect of a β-blocking product.

4.1. Guinea pig trachea

The $CD_{50}$'s before and after the addition of propranolol ($1.7 \times 10^{-8}$ mol=threshold dose) were determined for compound A and for Salbutamol (6 preparations per product).

For the two products, the $CD_{50}$ was multiplied by 3.5 under the inhibiting effect of propranolol.

| Product | $CD_{50}$ mol | | Ratio of $CD_{50}$ |
|---|---|---|---|
|  | Before propranolol | After propranolol |  |
| Compound A | $7.1 \times 10^{-8}$ | $2.5 \times 10^{-7}$ | 3.5 |
| Salbutamol | $1.1 \times 10^{-8}$ | $3.8 \times 10^{-8}$ | 3.5 |

4.2 Heart rate of the anesthetised dog

Acebutolol—Merck Index X-#13 (cardioselective $\beta_1$ blocking agent), at the dose of 0.5 mg/kg intravenously, completely antagonises the tachycardia caused by compound A, perfused for 6 minutes at the dose of 4.2 μg/kg and per min.

The results below are the averages of the values obtained in 3 dogs.

| Times |  | Heart rate | Variation |
|---|---|---|---|
| T 0 |  | 157 | — |
| T 0 + 1 min | ⎫ | 180 | +23 |
| T 0 + 2 min | ⎬ Perfusion | 197 | +40 |
| T 0 + 4 min | ⎬ compound A | 202 | +45 |
| T 0 + 6 min | ⎭ | 205 | +48 |
| = T 1 Inj. acebutolol |  |  |  |
| T 1 + 1 min |  | 162 | +5 |
| T 1 + 5 min |  | 156 | −1 |
| T 1 + 15 min |  | 149 | −8 |
| T 1 + 30 min |  | 147 | −10 |
| T 1 + 1 h |  | 154 | −3 |
| T 1 + 4 h |  | 143 | −14 |
| T 1 + 4 h 1 min | ⎫ | 146 | −11 |
| T 1 + 4 h 2 min | ⎬ Perfusion | 155 | −2 |
| T 1 + 4 h 4 min | ⎭ compound A | 160 | +3 |

-continued

| Times | Heart rate | Variation |
|---|---|---|
| T 1 + 4 h 6 min | 160 | +3 |

In conclusion, the results recorded above show that the compounds, studied in comparison with Salbutamol, possess:

a relaxant activity of the isolated trachea which is similar, a bronchodilator activity comparable by intravenous route, higher than or equal and of faster induction by intraduodenal route.

a comparable uterorelaxant activity, in vitro and in vivo, tachycardiac activity, in vitro, very much less, a tachycardiac activity orally which is lower in the anesthetised animal especially in an unanesthetised animal.

This group of results enables the therapeutic use of compounds to be contemplated, their selectivity on the bronchial adrenergic receptors and uterinereceptors ($\beta_2$) with respect to cardiac receptors ($\beta_1$) showing itself to be higher than that of Salbutamol.

Moreover, the speed of appearance of the bronchodilator effect enterally, combined with a satisfactory duration of action, contributes to the interest of these compounds.

We claim:

1. The compound (1-benzimidazolyl)-N-(2-(4-hydroxy-3-methoxy-phenyl)-2-hydroxy-ethyl)-3-amino butane corresponding to the following formula:

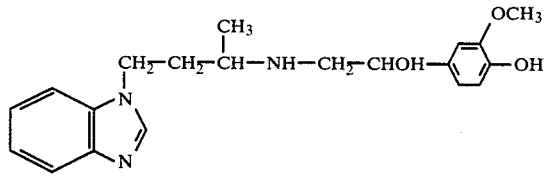

or a pharmaceutically acceptable, non-toxic, inorganic or organic acid addition salt, or a hydrate thereof.

2. Basic sulphate 1-[1-benzimidazolyl]-N-[2-(4-hydroxy-3-methoxy-phenyl)-2-hydroxy-ethyl]-3-amino butane basic sulphate or a hydrate thereof.

3. 1-[1-benzimidazolyl]-N-[2-(4-hydroxy-3-methoxy-phenyl)-2-hydroxy-ethyl]-3-amino butane dihydrochloride, or a hydrate thereof.

4. Pharmaceutical composition containing an effective amount of the beta-adrenergic compound 1-(1-benzimidazolyl)-N-(2-(4-hydroxy-3-methoxy-phenyl)-2-hydroxy-ethyl)-3-amino butane or a pharmaceutically acceptable, non-toxic, acid addition salt thereof or a hydrate of said salt, with a pharmaceutically acceptable, non-toxic carrier or vehicle.

5. Pharmaceutical composition according to claim 4, in tablet, capsule or dragee form suitable for oral administration, dosed with 0.5–10 mg of active principle, or syrup at a concentration of 0.1–2 mg/cm$^3$ of active principle.

6. Pharmaceutical composition according to claim 4, as an aqueous solution at a concentration of 0.02 to 0.4 mg/cm$^3$ of active principle, suitable for parenteral administration.

7. Pharmaceutical composition according to claim 4, in the form of a suppository containing 0.25 to 5 mg of active principle per unit.

8. Method of treating asthma or premature labor, comprising administering to the patient a physiologically effective amount of beta-adrenergic 1-(1-benzimidazolyl-N-(2-(4-hydroxy-3-methoxy-phenyl)-2-hydroxy-ethyl)-3-amino butane or a nontoxic acid addition salt thereof or a hydrate of said salt.

* * * * *